United States Patent
Nanko et al.

(10) Patent No.: US 10,718,305 B2
(45) Date of Patent: Jul. 21, 2020

(54) FUEL INJECTION PUMP

(71) Applicant: Yanmar Co., Ltd., Osaka-shi, Osaka-fu (JP)

(72) Inventors: Masaki Nanko, Osaka (JP); Yuji Shiba, Osaka (JP); Ryosuke Okamoto, Osaka (JP); Tetsu Hattori, Osaka (JP)

(73) Assignee: YANMAR CO., LTD., Osaka (JP)

( * ) Notice: Subject to any disclaimer, the term of this patent is extended or adjusted under 35 U.S.C. 154(b) by 7 days.

(21) Appl. No.: 15/779,477

(22) PCT Filed: Nov. 11, 2016

(86) PCT No.: PCT/JP2016/083546
§ 371 (c)(1),
(2) Date: May 25, 2018

(87) PCT Pub. No.: WO2017/090466
PCT Pub. Date: Jun. 1, 2017

(65) Prior Publication Data
US 2018/0335005 A1    Nov. 22, 2018

(30) Foreign Application Priority Data
Nov. 26, 2015 (JP) ................... 2015-231174

(51) Int. Cl.
*F02M 63/00* (2006.01)
*F02M 59/28* (2006.01)
(Continued)

(52) U.S. Cl.
CPC .......... *F02M 63/0001* (2013.01); *F01M 9/10* (2013.01); *F02D 1/02* (2013.01);
(Continued)

(58) Field of Classification Search
CPC ............... F02M 63/0001; F02M 41/06; F02M 41/1411; F02M 59/28; F02M 59/44;
(Continued)

(56) References Cited

U.S. PATENT DOCUMENTS 2,363,576 A * 11/1944 Devorak ................... F02D 1/00
137/627
2,503,458 A * 4/1950 Thaheld ............... F02M 59/462
417/502
(Continued)

FOREIGN PATENT DOCUMENTS

DE        10012306 A1 *  9/2001 ......... F02M 41/1405
EP        2876296 A1     5/2015
(Continued)

OTHER PUBLICATIONS

International Search Report dated Dec. 6, 1988 issued in corresponding PCT Application PCT/JP2016/083546 cites the patent documents above.
(Continued)

*Primary Examiner* — Sizo B Vilakazi
*Assistant Examiner* — Brian R Kirby
(74) *Attorney, Agent, or Firm* — Norton Rose Fulbright US LLP

(57) ABSTRACT

A fuel injection pump for a diesel engine, including: a control rack arranged in a rack chamber formed between a pump head and a pump housing, and configured to adjust a fuel injection amount; a transmission shaft rotatably supported by a transmission shaft hole formed in the pump housing; and a lubricating oil passage formed in the pump housing, and configured to pressure-feed lubricating oil between the transmission shaft and the transmission shaft hole. The transmission shaft has an oil passage therein through which passage the lubricating oil pressure-fed to the
(Continued)

lubricating oil passage partially passes, a first opening of the oil passage is communicated with the lubricating oil passage, and a second opening of the oil passage is formed on the outer circumferential surface of an upper portion of the transmission shaft, nearby the control rack.

20 Claims, 10 Drawing Sheets

(51) Int. Cl.
 *F02M 59/44*  (2006.01)
 *F01M 9/10*  (2006.01)
 *F02D 1/02*  (2006.01)
 *F02M 41/14*  (2006.01)
 *F02D 1/10*  (2006.01)
 *F02M 41/06*  (2006.01)
 *F02M 53/00*  (2006.01)
 *F02M 59/10*  (2006.01)
 *F02M 59/42*  (2006.01)

(52) U.S. Cl.
 CPC .............. *F02D 1/10* (2013.01); *F02M 41/06* (2013.01); *F02M 41/1411* (2013.01); *F02M 59/28* (2013.01); *F02M 59/44* (2013.01); *F02M 53/00* (2013.01); *F02M 59/102* (2013.01); *F02M 59/42* (2013.01)

(58) Field of Classification Search
 CPC ...... F02M 59/42; F02M 59/102; F02M 53/00; F02D 1/10; F02D 1/02; F01M 9/10
 USPC .................................. 123/364–367, 447–450
 See application file for complete search history.

(56) References Cited

U.S. PATENT DOCUMENTS

| | | | | |
|---|---|---|---|---|
| 2,828,727 A | * | 4/1958 | Fischer | F02M 41/1411 123/338 |
| 4,531,494 A | * | 7/1985 | Bailey | F02M 41/06 123/450 |
| 4,697,565 A | * | 10/1987 | Kobayashi | F02M 41/12 123/449 |
| 5,000,668 A | * | 3/1991 | Nakamura | F02M 41/121 123/449 |
| 5,007,400 A | * | 4/1991 | Babitzka | F02M 41/125 123/449 |
| 5,146,895 A | * | 9/1992 | Fehlmann | F02M 39/02 123/449 |
| 5,152,271 A | * | 10/1992 | Matsumura | F02D 41/3818 123/447 |
| 5,207,201 A | * | 5/1993 | Schlagmuller | F02M 41/12 123/447 |
| 5,619,971 A | * | 4/1997 | Kubo | F02M 41/1405 123/41.31 |
| 6,004,106 A | * | 12/1999 | Machida | F02M 39/02 417/223 |
| 6,286,485 B1 | * | 9/2001 | Felton | F02M 41/06 123/41.31 |
| 6,953,022 B1 | * | 10/2005 | Itsuki | F02D 1/025 123/364 |
| 8,714,940 B2 | * | 5/2014 | Nomura | F16H 61/0028 417/223 |
| 9,322,411 B2 | * | 4/2016 | Walder | F16D 1/108 |
| 2009/0163094 A1 | * | 6/2009 | Fukuoka | F01M 9/10 440/88 P |
| 2013/0133600 A1 | * | 5/2013 | Nagakura | F01M 9/10 123/90.34 |
| 2015/0093265 A1 | * | 4/2015 | Navas Sanchez | F02M 63/0001 417/271 |
| 2018/0335005 A1 | * | 11/2018 | Nanko | F02M 59/28 |

FOREIGN PATENT DOCUMENTS

| | | | | |
|---|---|---|---|---|
| JP | 1984-131970 U | | 9/1984 | |
| JP | 1988-125121 U | | 8/1988 | |
| JP | 03061663 A | * | 3/1991 | |
| JP | 1992-123367 U | | 11/1992 | |
| JP | 6-330833 A | | 11/1994 | |
| JP | H11166465 A | * | 6/1999 | |
| JP | 2000265917 A | * | 9/2000 | |
| JP | 2001115921 A | * | 4/2001 | |
| JP | 2007-303313 A | | 11/2007 | |
| JP | 2010159651 A | * | 7/2010 | ............ F04B 1/0413 |
| JP | 2013-204500 A | | 10/2013 | |
| JP | 2013204499 A | * | 10/2013 | |
| JP | 2013204500 A | * | 10/2013 | |
| WO | WO-2012097954 A1 | * | 7/2012 | ............ F04B 1/0448 |
| WO | WO-2013037545 A1 | * | 3/2013 | ............ F04B 1/0404 |
| WO | WO-2014063890 A1 | * | 5/2014 | ............ F02M 59/102 |

OTHER PUBLICATIONS

Extended European Search Report dated Oct. 30, 2018 for EP Application No. 16868414, citing the art herein.

\* cited by examiner

FIG. 8A
FIG. 8B
FIG. 8C
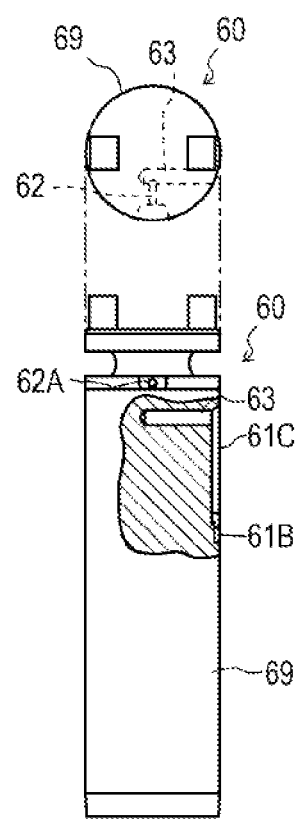
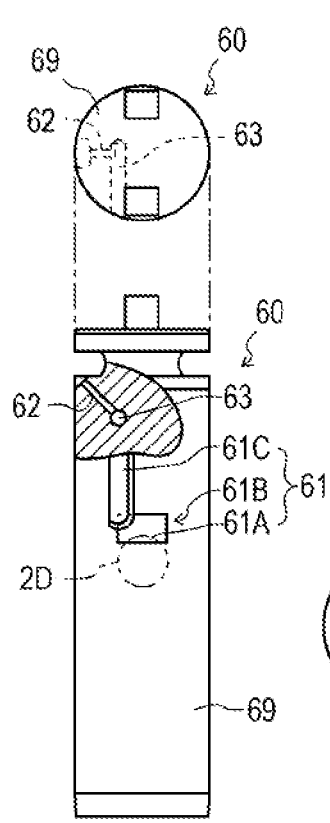
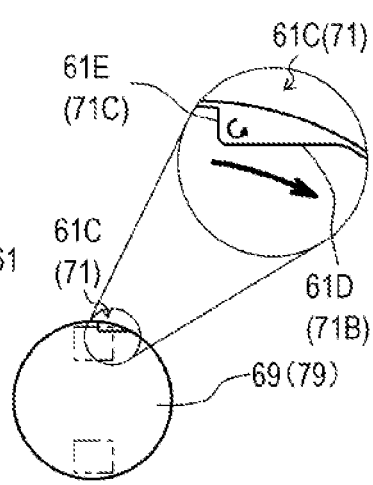

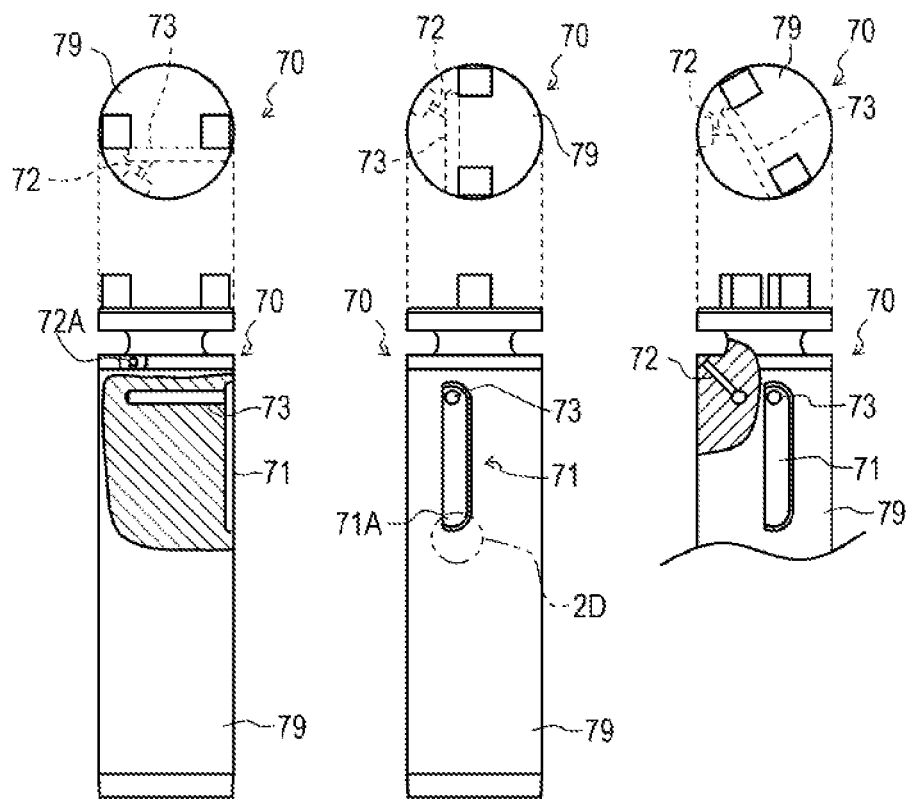

FUEL INJECTION PUMP

CROSS REFERENCES TO RELATED APPLICATIONS

This application is a national stage application pursuant to 35 U.S.C. 371 of International Application No. PCT/JP2016/083546, filed on Nov. 11, 2016, which claims priority under 35 U.S.C. § 119 to Japanese Patent Application No. 2015-231174, filed on Nov. 26, 2015, the disclosures of which are hereby incorporated by reference in their entireties.

TECHNICAL FIELD

The present invention relates to a technology of a fuel injection pump.

BACKGROUND ART

Traditionally, there has been known a fuel injection pump of an engine in which a control rack is disposed in a rack chamber surrounded by a portion of the upper surface of a pump housing forming an indentation and an under surface of a pump head (e.g., see Patent Literature 1, PTL 1). Operating the control rack enables adjustment of a fuel supply amount from a fuel injection pump to a cylinder.

The fuel injection pump changes a movement amount of the control rack according to the temperature state of the engine, to improve a start characteristic of the engine. However, when moisture contained in the blow-by gas entering from the engine condenses and adheres to the control rack, the moisture is frozen on the control rack when the temperature around the control rack falls below the freezing point. As a result, there is a possibility that the control rack cannot move due to ice droplets, and that fuel cannot be supplied to the engine.

CITATION LIST

Patent Literature

PTL 1: Japanese Patent Application Laid-Open No. 2013-204500

SUMMARY OF INVENTION

Technical Problem

A technical problem to be addressed by the present invention is to provide a fuel injection pump which prevents failure in starting an engine due to frozen moisture adhered to the control rack.

Solution to Problem

A fuel injection pump according to an aspect of the present invention is a fuel injection pump provided in an engine, including: a control rack arranged in a rack chamber formed between a pump head and a pump housing, the control rack being configured to adjust a fuel injection amount; a transmission shaft rotatably supported by a transmission shaft hole formed in the pump housing; and a lubricating oil passage formed in the pump housing, the lubricating oil passage being configured to pressure-feed lubricating oil between the transmission shaft and the transmission shaft hole, wherein the transmission shaft has an oil passage formed therein, through which passage the lubricating oil pressure-fed to the lubricating oil passage partially passes, a first opening of the oil passage is communicated with the lubricating oil passage, and a second opening of the oil passage is formed on an outer circumferential surface of an upper portion of the transmission shaft, nearby the control rack.

The fuel injection pump of the aspect of the present invention is preferably such that the oil passage includes: a groove formed in the outer circumferential surface of the transmission shaft in an axial direction, the groove including the first opening; a communication path opened on a wall portion of the groove, and formed in a radial direction of the transmission shaft; and a supply hole communicated with the communication path, and formed from substantially an axial center portion of the transmission shaft to the second opening.

The fuel injection pump of the aspect of the present invention is preferably such that the groove has at least one side wall formed perpendicular to the wall portion.

The fuel injection pump of the aspect of the present invention is preferably such that a lower end portion of an open portion of the groove is formed in a substantially U-shape.

Advantageous Effects of Invention

A fuel injection pump of the aspect of the present invention can prevent failure in starting an engine due to freezing of the control rack.

BRIEF DESCRIPTION OF DRAWINGS

FIG. 8A, FIG. 8B and FIG. 8C are diagrams showing a structure of an oil passage of a third embodiment.

FIG. 9A, FIG. 9B and FIG. 9C are diagrams showing a structure of an oil passage of a fourth embodiment.

DESCRIPTION OF EMBODIMENT

Figure 1:
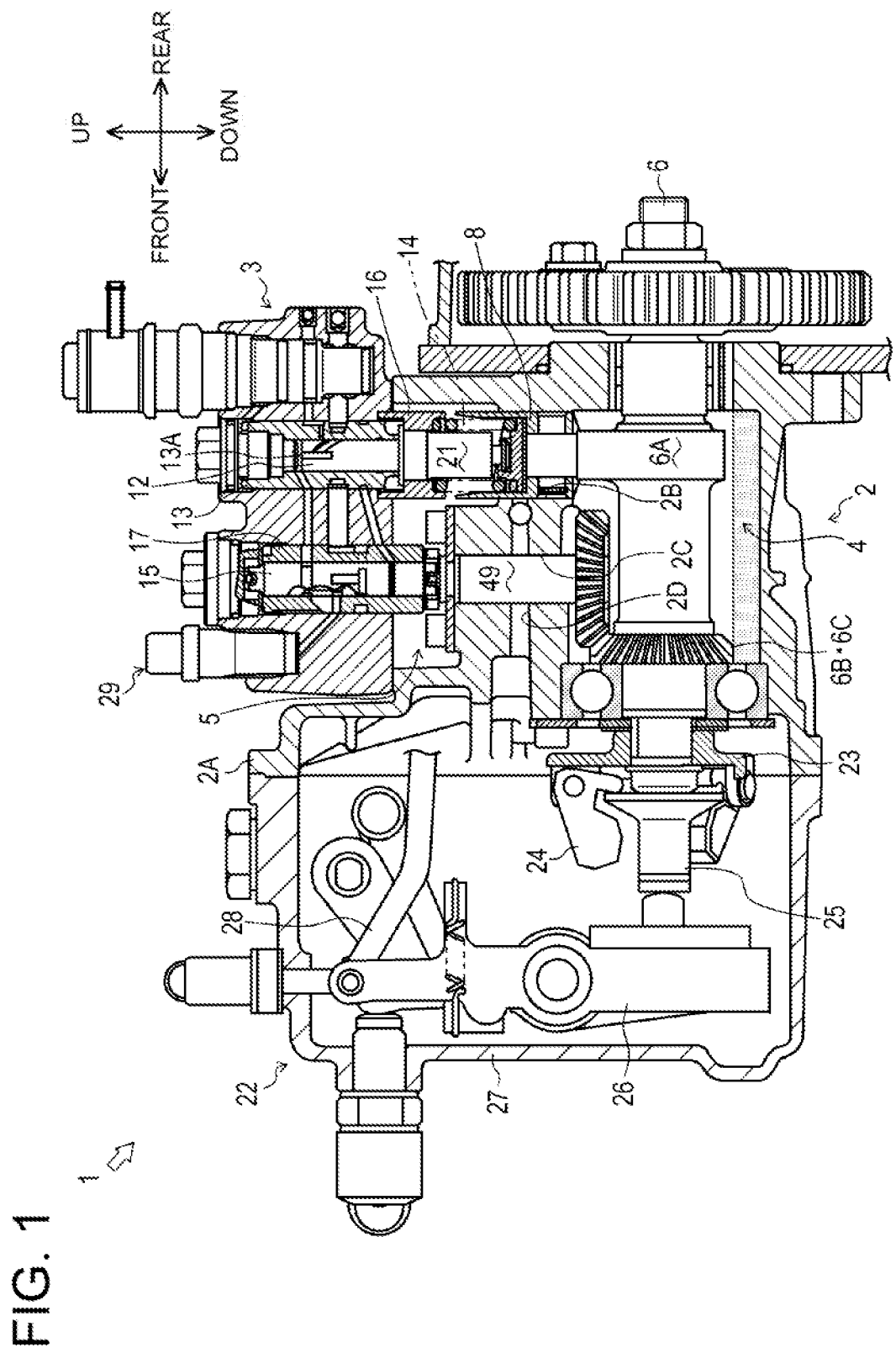
FIG. 1 is a side cross sectional view showing a structure of a fuel injection pump.
Figure 2:
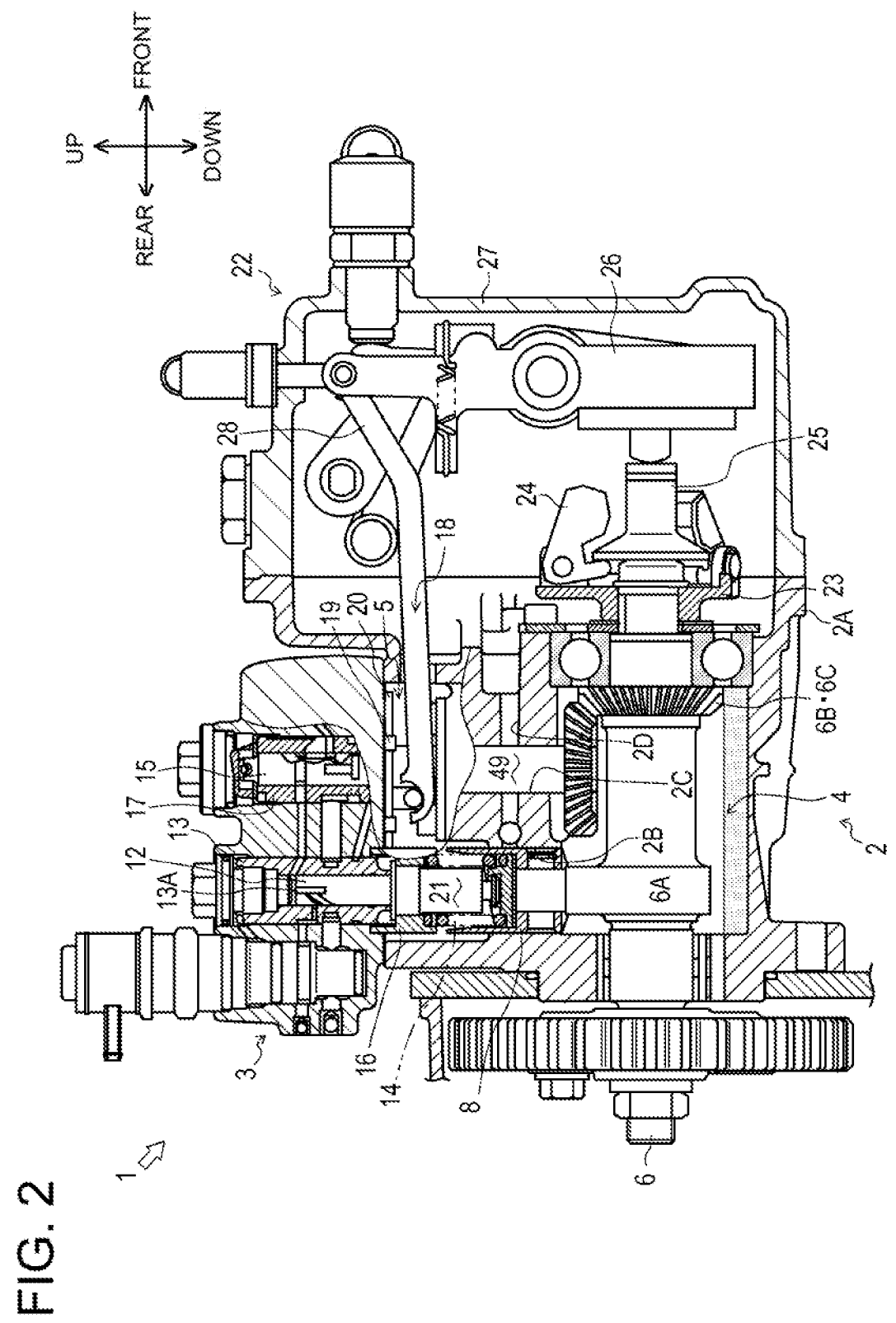
FIG. 2 is another side cross sectional view showing the structure of the fuel injection pump.
Figure 3:
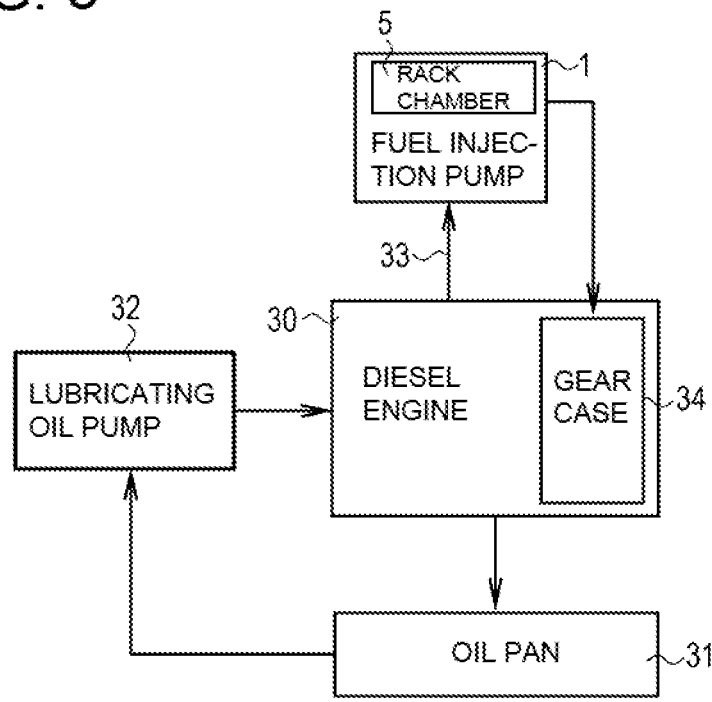
FIG. 3 is a block diagram showing a lubricating oil supply path in a diesel engine and a fuel injection pump.
Figure 4:
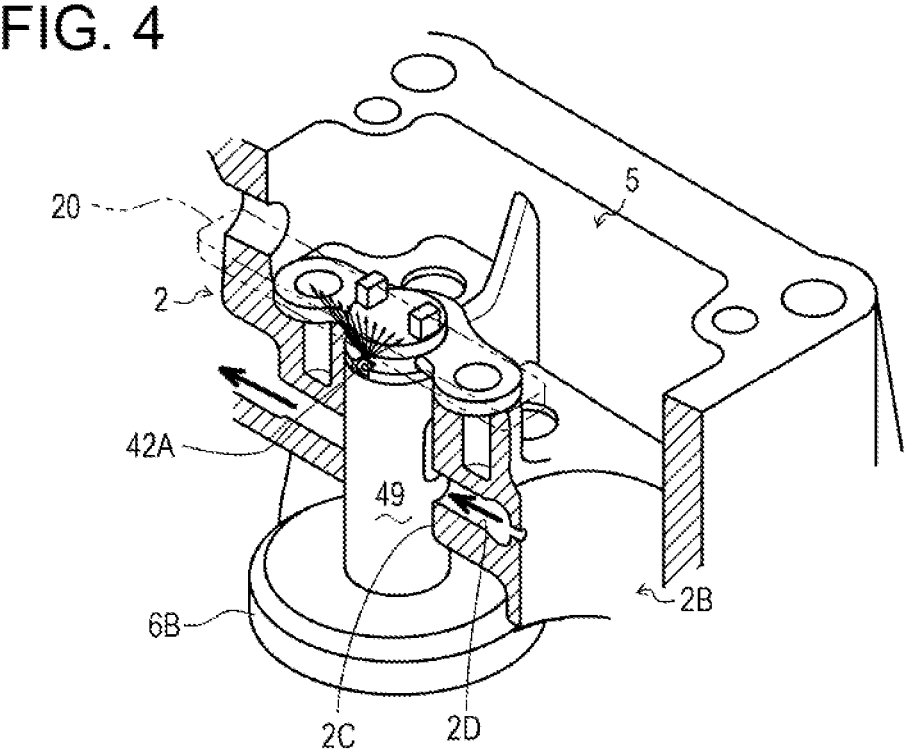
FIG. 4 is a partial cross-sectional perspective view showing a transmission shaft and a pump housing which supports the transmission shaft.

The following describes a structure of a fuel injection pump 1, with reference to FIG. 1 to FIG. 3.

It should be noted that, in side views of FIG. 1 and FIG. 2, the structure of the fuel injection pump 1 is partially illustrated in a cross-sectional view.

The fuel injection pump 1 is for supplying fuel to a not-shown fuel injection nozzle of a diesel engine 30. The fuel injection pump 1 is a so-called distribution type fuel injection pump which distributes and supplies fuel to each cylinder of the diesel engine 30.

The following description on the fuel injection pump 1 related to the present invention, the front-rear direction refers to the axial direction of a later-described cam shaft 6, and the front side refers to the side on which a later-described governor device 22 is disposed, whereas the rear side refers to a side on which a later-described gear case 34.

As shown in FIG. 1 and FIG. 2, the fuel injection pump 1 includes a pump housing 2 and a pump head 3.

The pump housing 2 is a structure constituting the lower half of the fuel injection pump 1. In a plane of the pump housing 2, a substantially parallelepiped indentation recessed downward is formed. In a lower portion of the pump housing 2, a cam chamber 4 is formed. The cam chamber 4 is structured so that the cam shaft 6 is arranged, and oil having lubricated the inside of the pump housing 2 can be stored.

The pump housing 2 has a governor flange 2A to which the governor device 22 is attached, which is integrally formed with the pump housing 2. To the pump housing 2, the cam shaft 6, a tappet 8, a transmission shaft 49, and the like are assembled.

The pump head 3 is a structure constituting the upper half of the fuel injection pump 1. The pump head 3 is fixed on the pump housing 2. A space surrounded by a portion of the upper surface of the pump housing 2 forming the indentation and an under surface of the pump head 3 constitutes a rack chamber 5. The rack chamber 5 is arranged above the cam chamber 4. To the pump head 3, a plunger 12, a plunger barrel 13, a spring 14, a distribution shaft 15, a sleeve 17, an amount adjusting mechanism 18, and the like are assembled.

The cam shaft 6 is a long member having a substantially cylindrical shape, which is bridged horizontally in the cam chamber 4. The cam shaft 6 is rotatably supported by the pump housing 2 through a bearing or the like. To a midway portion of the cam shaft 6, a cam 6A which drives the plunger 12 is fixed.

The tappet 8 is a substantially cylindrical member whose lower end portion is closed. The tappet 8 is slideably fit in a tappet hole 2B formed in the pump housing 2. The tappet hole 2B is a hole formed so as to penetrate the pump housing 2 between the cam chamber 4 and the rack chamber 5 in the vertical direction and is mostly closed by the tappet 8.

The transmission shaft 49 is a substantially cylindrical member supported by the pump housing 2. The transmission shaft 49 is slideably fit in a transmission shaft hole 2C formed in the pump housing 2. The transmission shaft hole 2C is a hole formed so as to penetrate the pump housing 2 between the cam chamber 4 and the rack chamber 5 in the vertical direction and is mostly closed by the transmission shaft 49. The transmission shaft 49 is arranged above the cam shaft 6 so that its axial direction is perpendicular to the cam shaft 6. An upper end portion of the transmission shaft 49 protrudes into the rack chamber 5 and is connected to the distribution shaft 15 in the rack chamber 5. The transmission shaft 49 is connected to the cam shaft 6 in an interlocking manner, through bevel gears 6B and 6C provided at a lower end portion of the transmission shaft 49.

The distribution shaft 15 is a substantially cylindrical member supported by the pump head 3. The distribution shaft 15 is rotatably fit in a sleeve 17 fixed to the pump head 3. The distribution shaft 15 is arranged above the transmission shaft 49 so that its axial direction is perpendicular to the cam shaft 6. The distribution shaft 15 is connected to the transmission shaft 49 in an interlocking manner.

As shown in FIG. 2, the amount adjusting mechanism 18 is a mechanism for adjusting a fuel amount supplied from the fuel injection pump 1 to each cylinder of the diesel engine 30. The amount adjusting mechanism 18 includes a rack guide 19, a control rack 20, and a control sleeve 21.

The rack guide 19 is a member that supports the control rack 20. The rack guide 19 is fixed in the front-rear direction on the upper surface of the rack chamber 5 and on the left side of the transmission shaft 49. In the rack guide 19, a through hole for letting the control rack 20 penetrate therethrough.

The control rack 20 is a rod-like member. The control rack 20 is penetrated through the through hole of the rack guide 19. The control rack 20 is capable of sliding inside the through hole of the rack guide 19. One end portion of the control rack 20 is connected to the control sleeve 21, and a midway portion of the control rack 20 is connected to a link 28 of the later-described governor device 22 through a pin or the like.

The control sleeve 21 is a substantially cylindrical member. The control sleeve 21 is fitted to the plunger 12, while being sandwiched between the plunger 12 and a spring receiver 16. The control sleeve 21 is rotatable in a circumferential direction, along the inner circumferential surface of the spring receiver 16. At this time, the plunger 12 rotates integrally with the control sleeve 21 as the control sleeve 21 rotates.

The governor device 22 is a device for activating the amount adjusting mechanism 18. The governor device 22 includes a support member 23, a plurality of centrifugal weights 24, 24, . . . , a slide member 25, a governor arm 26, a governor housing 27, a link 28, and the like. The governor housing 27 containing these members is attached to the governor flange 2A using a bolt or the like.

The following describes an operation mode of the fuel injection pump 1 having the above-described structure.

When the cam shaft 6 rotates, the tappet 8 abutting the cam 6A reciprocates in the vertical direction in the tappet hole 2B. Along with this, the plunger 12 reciprocates in the plunger barrel 13 in the vertical direction. This way, fuel is sucked into the pressurizing chamber 13A and pressurized, and then supplied to the distribution shaft 15.

The distribution shaft 15 is rotated with rotation of the cam shaft 6, through the bevel gears 6B, 6C and the transmission shaft 49. The fuel supplied to the distribution shaft 15 is supplied to a delivery valve 29 by the rotation of the distribution shaft 15. The fuel supplied to the delivery valve 29 is injected from a fuel injection nozzle of each cylinder through a not-shown injection pipe.

In the governor device 22, the centrifugal weights 24, 24, . . . that rotate integrally with the cam shaft 6 cause the slide member 25 to move according to the magnitude of the centrifugal force generated. The movement of the slide member 25 rotates the governor arm 26 around the support shaft. The rotation of the governor arm 26 moves the link 28. The movement of the link 28 moves the control rack 20 in the through hole of the rack guide 19. The movement of the control rack 20 causes the control sleeve 21 and the plunger 12 to rotate in a circumferential direction. This way, an amount of fuel to be supplied from the fuel injection pump 1 to each cylinder is adjusted.

The following describes circulation of the lubricating oil, with reference to FIG. 3.

The lubricating oil for the diesel engine 30 and the fuel injection pump 1 is stored in an oil pan 31. The lubricating oil stored in the oil pan 31 is sucked up by a lubricating oil pump 32 and is supplied to the diesel engine 30 through a not-shown oil filter or the like. The lubricating oil supplied to the diesel engine 30 is supplied to each part of the diesel engine 30 through a not-shown lubricating oil passage formed in the diesel engine 30. The lubricating oil having lubricated the diesel engine 30 is returned to the oil pan 31.

Part of the lubricating oil supplied to the diesel engine 30 is supplied to the fuel injection pump 1 through a lubricating oil passage 33. The lubricating oil supplied to the fuel injection pump 1 lubricates the amount adjusting mechanism 18 and the cam shaft 6 inside the pump housing 2, and then discharged to the gear case 34 of the diesel engine 30. The lubricating oil discharged to the gear case 34 is returned to the oil pan 31.

As shown in FIG. 1 to FIG. 4, part of the lubricating oil supplied to the fuel injection pump 1 is pressure-fed between the transmission shaft 49 and the transmission shaft hole 2C, through a lubricating oil passage 2D. The lubricating oil passage 2D is an oil passage for pressure-feeding part of the lubricating oil supplied to inside the pump housing 2, between the transmission shaft 49 and the transmission shaft hole 2C. The lubricating oil passage 2D penetrates from a wall surface of the tappet hole 2B to a wall surface on the side of the governor housing 27, in the pump housing 2. A midway portion of the lubricating oil passage 2D communicates with the transmission shaft hole 2C.

In the above-described structure, part of the lubricating oil supplied from the diesel engine 30 to the fuel injection pump 1 is pressure-fed between the transmission shaft 49 and the transmission shaft hole 2C through the lubricating oil passage 2D, thereby reducing the friction force and wear occurring due to sliding movement of the transmission shaft 49 and the transmission shaft hole 2C. The part of lubricating oil pressure-fed between the transmission shaft 49 and the transmission shaft hole 2C is fed to the downstream side of the lubricating oil passage 2D with the rotation of the transmission shaft 49 and is supplied to the governor housing 27.

The following describes a structure of the transmission shaft 49, with reference to FIG. 5A through FIG. 6B.

Figure 5A:
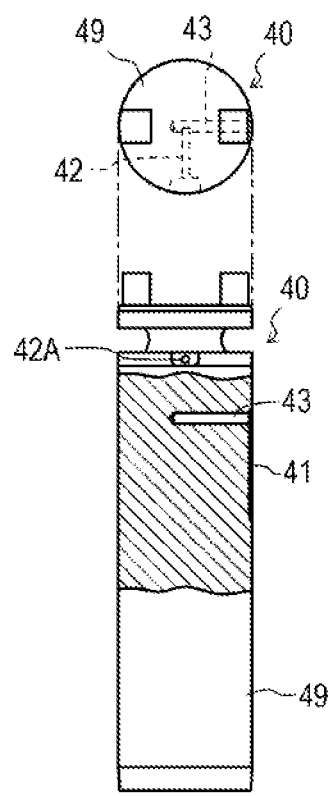
FIG. 5A and FIG. 5B are diagrams showing a structure of an oil passage of a first embodiment.
Figure 5B:
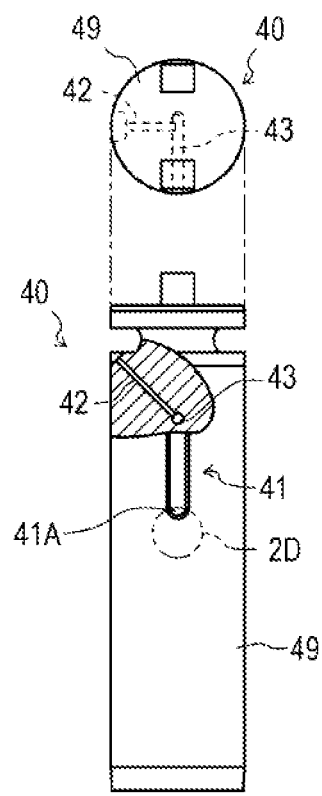

It should be noted that FIG. 5A provides a front view (view from the side of the later-described second opening 42A) and a plan view of the structure of the transmission shaft 49, whereas FIG. 5B provides a side view (view from the side of the later-described first opening 41) and a plan view of the structure of the transmission shall 49.

Figure 6A:
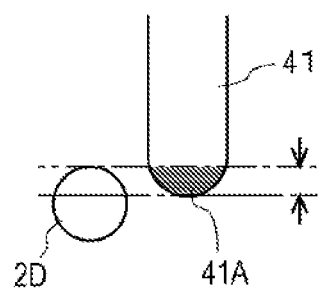
FIG. 6A is a diagram showing a first opening of the oil passage.
Figure 6B:
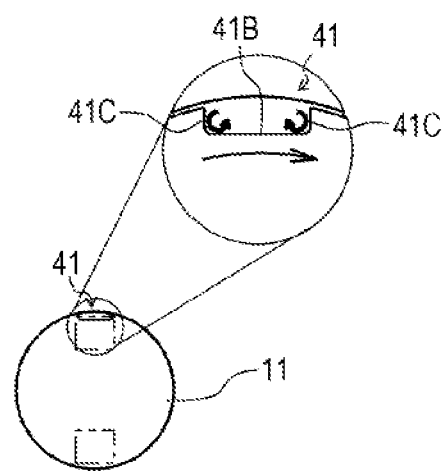
FIG. 6B is a plan view showing a direction in which the lubricating oil flows in the groove of the oil passage.

Further, FIG. 6A provides a schematic side view of the first opening 41A, whereas FIG. 6B provides a schematic plan view of the groove 41.

As shown in FIG. 5A and FIG. 5B, the transmission shaft 49 is a first embodiment related to the transmission shaft of the present invention. The transmission shaft 49 has an oil passage 40 formed therein, through which passage the lubricating oil pressure-fed to the lubricating oil passage 2D partially passes. The oil passage 40 includes: the groove 41 formed in the outer circumferential surface of the transmission shaft 49 in an axial direction, the groove 41 including the first opening 41A; the communication path 43 opened on a wall portion 41B (see FIG. 6A and FIG. 6B of the groove 41, and formed in a radial direction of the transmission shaft 49; and a supply hole 42 communicated with the communication path 43, and formed from substantially an axial center portion of the transmission shaft 49 to the second opening 42A. The first opening 41A of the oil passage 40 is communicated with the lubricating oil passage 2D, and the second opening 42A of the oil passage 40 is formed on an outer circumferential surface of an upper portion of the transmission shaft 49, nearby the control rack 20 (see FIG. 4).

Part of the lubricating oil pressure-fed to the lubricating oil passage 2D is taken into the oil passage 40 through the first opening 41A, and then passes through the oil passage 40, and injected into the control rack 20 through the second opening 42A.

The groove 41 is formed vertically long shape, in a predetermined portion of the outer circumferential surface of the transmission shaft 49. The first opening 41A is formed by partially overlapping the groove 41 with the lubricating oil passage 2D, in the axial direction. More specifically, with the lower end portion of the groove 41A overlapping with the upper portion of the lubricating oil passage 2D in the vertical direction, the first opening 41A for taking in the lubricating oil from the lubricating oil passage 2D is formed. In the present example, the first opening 41A is a part of the groove 41, and by having the groove 41 overlapped with the lubricating oil passage 2D in the axial direction, the first opening 41A is formed.

In the above-described structure, while the transmission shaft 49 rotates once, the groove 41 communicates once with the upstream side of the lubricating oil passage 2D. With the rotation of the transmission shaft 49, the first opening 41A constituting the groove 41A is communicated with the lubricating oil passage 2D. This way, part of the lubricating oil pressure-fed to the lubricating oil passage 2D is intermittently taken into the groove 41 through the first opening 41A.

It should be noted that the amount of lubricating oil taken into the oil passage 40 through the first opening 41A during a single rotation of the transmission shaft 49 is determined based on the time and area of communication between the lubricating oil passage 2D and the first opening 41A.

The communication path 43 is structured as a passage communicating the groove 41 and the supply hole 42. An end portion (upper end portion) of the groove 41 and the start portion (an end portion on the side of the axial center of the transmission shaft 49) of the supply hole 42 are substantially at the same level, and the start portion of the supply hole 42 is positioned substantially at the axial center portion of the transmission shaft 49. In the above-described structure, the communication path 43 is formed as a lateral hole extended toward the substantially axial center portion of the transmission shaft 49 and is arranged at substantially the same level as the end portion of the groove 41. The communication path 43 is provided as a lateral hole from the later-described wall portion 41B of the groove 41 to the inside of the transmission shaft 49. Therefore, the communication passage 43 can be easily formed without a need for complicated processing.

The supply hole 42 is for spraying the lubricating oil taken in from the first opening 41A through the communication path 43 to the control rack 20 provided on the upper surface of the rack chamber 5. The supply hole 42 is a hole extended toward substantially the axial center portion of the transmission shaft 49, from the second opening 42A provided in the outer circumferential surface of the upper portion of the transmission shaft 49, nearby the control rack 20.

The cross-sectional area of the supply hole 42 (the cross-sectional area relative to the direction of the flow of the lubricating oil) is smaller than the cross-sectional area of the communication path 43 (the cross-sectional area relative to the direction of the flow of the lubricating oil). By changing the size of the cross-sectional area of the supply hole 42, the pressure of the lubricating oil flowing in the supply hole 42 can be changed. By forming the supply hole 42 so that its cross-sectional area is smaller than the cross-sectional area of the communication path 43, the pressure of the lubricating oil flowing in the supply hole 42 is made a pressure that allows spraying of the lubricating oil to the control rack 20. In the present embodiment, the supply hole 42 is formed by a drilled hole or the like.

The supply hole 42 is inclined at a desirable inclination angle toward the inside of the transmission shaft 49, from the second opening 42A formed in the outer circumferential surface of the upper portion of the transmission shaft 49, nearby the control rack 20, considering the relative positions of the transmission shaft 49 and the control rack 20 and the pressure of the lubricating oil flowing inside the supply hole 42, so that the lubricating oil can be sprayed to the control rack 20.

The second opening 42A is provided in the outer circumferential surface of the upper portion of the transmission shaft 49, and in a position that allows spraying of the lubricating oil to the control rack 20, at a time of injection. In the present embodiment, the second opening 42A is provided in a position rotated and displaced from the position of the first opening 41A, by a desirable angle between approximately 90 to 135 degrees (approximately 90 degrees in the present embodiment) towards the downstream side of the rotation of the transmission shaft 49, considering the oil pressure of the lubricating oil flowing in the oil passage 40, the relative positions of the transmission shaft 49 and the control rack 20, and the like.

In the above-described structure, when the transmission shaft 49 rotates, the lubricating oil passage 2D and the groove 41 are communicated with each other, and the oil is taken into the groove 41 through the first opening 41A. The lubricating oil taken into the groove 41 is supplied to the supply hole 42 through the communication path 43. The lubricating oil supplied to the supply hole 42 is injected at a predetermined position and is sprayed onto the control rack 20.

As described, by spraying part of the lubricating oil in the lubricating oil passage 2D onto the control rack 20, the moisture adhered to the control rack 20 is removed. That is, even if the temperature of the rack chamber 5 of the fuel injection pump 1 becomes equal to or lower than the dew point temperature of the blow-by gas, moisture does not adhere to the control rack 20 disposed inside the rack chamber 5. At the same time, even if the temperature of the rack chamber 5 becomes equal to or lower than the freezing point, start failure of the diesel engine 30 due to freezing of the control rack 20 can be prevented.

As shown in FIG. 6A the lower end portion of the first opening 41A constituting the groove 41 is formed into a substantially U-shape. The lower end portion of the groove 41 is curved in a substantially U-shape, and this lower end portion is arranged to overlap the lubricating oil passage 2D.

With the substantially U-shaped lower end portion of the groove 41, the time and area of communication between the lubricating oil passage 2D and the first opening 41A can be reduced. Further, by making the portion of the groove 41 formed into a substantially U-shape communicable with the upper portion of the lubricating oil passage 2D, the time and area of communication between the lubricating oil passage 2D and the first opening 41A can be further reduced.

As described, by reducing the time and area of communication between the lubricating oil passage 2D and the first opening 41A which are communicated with each other while the transmission shaft 49 rotates once, the amount of lubricating oil to be taken in through the first opening 41A can be adjusted at a time of rotating the transmission shaft 49 at a high speed. Therefore, the amount of the lubricating oil sprayed through the supply hole 42 within a certain period can be made substantially constant, irrespective of the rotational speed of the transmission shaft 49.

The following describes the shape of the groove 41, with reference to FIG. 6B.

The groove 41 has a wall portion 41B forming a bottom of the groove 41, and side walls 41C formed substantially perpendicularly to the wall portion 41B, which are provided on circumferential end portions of the wall portion 41B. That is, the groove 41 is formed in a substantially U-shape in plan view. In the wall portion 41B of the groove 41, the communication path 43 is formed in a radial direction of the transmissions shaft 49.

With the side walls 41C of the groove 41 formed substantially perpendicularly to the wall portion 41B of the groove 41, the lubricating oil taken into the groove 41 from the first opening 41A forms vortices at corner portions formed by the wall portion 41B and the side walls 41C of the groove 41. Since the lubricating oil tends to stay at the corner portions of the groove 41, leakage of the lubricating oil from the groove 41 between the transmission shaft hole 2C and the transmission shaft 49 can be reduced, and the oil pressure of the lubricating oil flowing in the groove 41 can be maintained.

The following describes structures of transmission shafts of embodiments with reference to FIG. 7A through FIG. 9C.

An oil passage provided in the transmission shaft of each of the embodiments shown in FIG. 7A through FIG. 9C is structured so that a total length of its injection hole is shorter, as compared with the oil passage 40 of the embodiment shown in FIG. 5A and FIG. 5B.

A structure of a transmission shaft 59 is described with reference to FIG. 7A and FIG. 7B. The transmission shaft 59 is a second embodiment related to the transmission shaft of the present invention. The transmission shaft 59 has an oil passage 50 formed therein, through which passage the lubricating oil pressure-fed to the lubricating oil passage 2D partially passes.

Figure 7A:
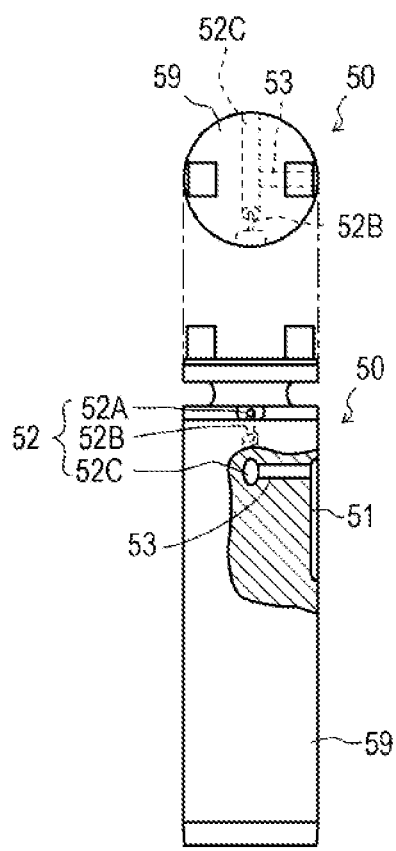
FIG. 7A and FIG. 7B are diagrams showing a structure of an oil passage of a second embodiment.
Figure 7B:
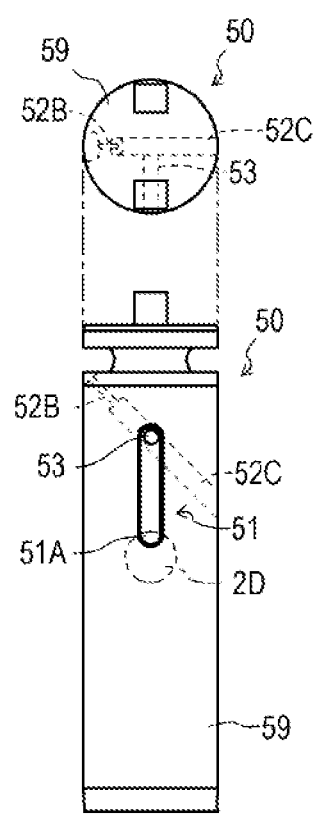

It should be noted that FIG. 7A provides a front view (view from the side of the later-described second opening 52) and a plan view of the structure of the transmission shaft 59, whereas FIG. 7B provides a side view (view from the side of the later-described first opening 51A) and a plan view of the structure of the transmission shaft 59.

The groove 51 is formed as an upright groove provided in an axial direction, in the outer circumferential surface of the transmission shaft 59. A first opening 51A is formed by having the upper portion of the lubricating oil passage 2D overlapped with the lower end portion of the groove 51. In the present embodiment, the second opening 52A is provided in a position rotated and displaced from the position of the first opening 51A, by a desirable angle between approximately 90 to 135 degrees (approximately 90 degrees in the present embodiment) towards the downstream side of the rotation of the transmission shaft 59. In the present example, the first opening 51A is a part of the groove 51, and by having the groove 51 overlapped with the lubricating oil passage 2D in the axial direction, the first opening 51A is formed.

The supply hole 52 is a hole penetrating the transmission shaft 59, substantially through the axial center portion, from the second opening 52A provided in the outer circumferential surface of the upper portion of the transmission shaft 59, nearby the control rack 20. The supply hole 52 is formed as a hole 52B constituted by a drilled hole and the like from the second opening 52A to a middle portion between the second opening 52A and substantially the axial center portion of the transmission shaft 59, and is formed as a through hole 52C from the middle portion between the second opening 52A and substantially the axial center portion of the transmission shaft 59 to the outer circumferential surface of the transmission shaft 59 opposed to the second opening 52A, in plan view of the transmission shaft 59. The diameter of the through hole 52C is larger than that of the hole 52B.

The hole 52B is formed from the second opening 52A, and the through hole 52C is formed from the outer circumferential surface of the transmission shaft 59, opposed to the second opening 52B in a plan view. In the midway portion through hole 52C, a communication path 53 communicating with the upper end portion of the groove 51 is formed.

As hereinabove described, by forming the through hole 52C from the outer circumferential surface of the transmission shaft 59 opposed to the second opening 52A, the communication path 53 and the start portion of the hole 52B can be easily communicated with each other, and the oil passage 50 can be structured so that the total length of the hole 52B constituting the supply hole 52 is short. Further, since the opening of the outer circumferential surface of the transmission shaft 59 opposed to the second opening 52A is substantially sealed by the transmission shaft hole 2C, the oil pressure of the lubricating oil flowing in the oil passage 50 can be maintained.

As described, by making the total length of the hole 52B constituting the supply hole 52 short, as compared to the oil passage 40 of the embodiment shown in FIG. 5A and FIG. 5B, machining is made easier, and the life of a machining tool is made longer.

A structure of a transmission shaft 69 is described with reference to FIG. 8A, through FIG. 8C. The transmission shaft 69 is a third embodiment related to the transmission shaft of the present invention. The transmission shaft 69 has an oil passage 60 formed therein, through which passage the lubricating oil pressure-fed to the lubricating oil passage 2D partially passes.

It should be noted that. FIG. 8A provides a front view (view from the side of the later-described second opening 62) and a plan view of the structure of the transmission shaft 69, whereas FIG. 8B provides a side view (view from the side of the later-described first opening 61A) and a plan view of the structure of the transmission shaft 69. FIG. 8C shows a plan view of an upright groove 61C constituting the later-described oil passage 60.

The supply hole 62 is formed substantially towards the axial center portion from the second opening 62A provided in the outer circumferential surface of the upper portion of the transmission shaft 69, nearby the control rack 20. The start portion of the supply hole 62 (an end portion on the side of the axial center of the transmission shaft 69) is positioned in a middle portion between the outer circumferential surface of the upper portion of the transmission shaft 69 (second opening 62A) and substantially the axial center portion of the transmission shaft 69. The supply hole 62 is formed by a drilled hole or the like.

The groove 61 includes: the upright groove 61C provided in the axial direction in the outer circumferential surface of the transmission shaft 69 and a lateral groove 61B provided so as to partially overlap with the lower end portion of the upright groove 61C in the circumferential direction of the transmission shaft 69. The first opening 61A is formed by providing the lateral groove 61B so as to communicate with the lubricating oil passage 2D. The lateral groove 61B is arranged so that its rotation-downstream end overlaps with a rotation-upstream end of the upright groove 61C. The upright groove 61C is arranged closer to the supply hole 62 as compared to the groove 41 of the embodiment shown in FIG. 5A and FIG. 5B. A lateral hole serving as a communication path 63 is provided from the upper end portion of the upright groove 61C toward the start portion of the supply hole 62. In the present example, the first opening 61A is a part of the lateral groove 61B, and by having the lateral groove 61B overlapped with the lubricating oil passage 2D in the axial direction, the first opening 61A is formed.

The following describes the shape of the upright groove 61C, with reference to FIG. 8C.

The upright groove 61C has a wall portion 61D forming a bottom of the upright groove 61C, and a side wall 61E formed substantially perpendicularly to the wall portion 61D, which is provided only to the rotation-upstream end of the wall portion 61D. That is, the upright groove 61C is formed in a substantially L-shape in plan view. The communication path 63 is a lateral hole formed in a radial direction of the transmission shaft 69 from the wall portion 61D of the upright groove 61C.

With at least one side wall 61E formed substantially perpendicularly to the wall portion 61D, the lubricating oil taken into the upright groove 61C from the first opening 61A forms a vortex at a corner portion formed by the wall portion 61D and the side wall 61E of the groove 61C. Since the lubricating oil tends to stay at the corner portion of the upright groove 61C, leakage of the lubricating oil from the upright groove 61C between the transmission shaft hole 2C and the transmission shaft 69 can be reduced, and the oil pressure of the lubricating oil flowing in the upright groove 61C can be maintained.

Further, the communication path 63 is provided as a lateral hole from the wall portion 61D of the upright groove 61C to the inside of the transmission shaft 69. Therefore, the communication passage 63 can be easily formed without a need for complicated processing.

Further, by providing the lateral groove 61B so as to overlap with the lower end portion of the upright groove 61C in the circumferential direction, and structuring the first opening 61A so that the lateral groove 61B and the lubricating oil passage 2D are communicated with each other, the second opening 62A is provided in a position rotated and displaced from the position of the first opening 61A, by a desirable angle between approximately 90 to 135 degrees (approximately 90 degrees in the present embodiment) towards the downstream side of the rotation of the transmission shaft 69. Therefore, the lubricating oil can be sprayed from the second opening 62A onto the control rack 20, at a desirable position.

As described, by making the total length of the supply hole 62 short, as compared to the oil passage 40 of the embodiment shown in FIG. 5A and FIG. 5B, machining is made easier, and the life of a machining tool is made longer.

A structure of a transmission shaft 79 is described with reference to FIG. 9A through FIG. 9C. The transmission shaft 79 is a fourth embodiment related to the transmission shaft of the present invention. The transmission shaft 79 has an oil passage 70 formed therein, through which passage the lubricating oil pressure-fed to the lubricating oil passage 2D partially passes.

It should be noted that FIG. 9A provides a front view (view from the side of the later-described second opening 72A) and a plan view of the structure of the transmission shaft 79. FIG. 9B provides a side view (view from the side of the later-described first opening 71A) and a plan view of the structure of the transmission shaft 79, and FIG. 9C provides a view of the structure of the transmission shaft 79 seen from a direction perpendicular to the axial direction of the later-described supply hole 72.

The supply hole 72 is formed substantially towards the axial center portion from the second opening 72A provided in the outer circumferential surface of the upper portion of the transmission shaft 79, nearby the control rack 20. The start portion of the supply hole 72 (an end portion on the side of the axial center of the transmission shaft 79) is positioned in a middle portion between the outer circumferential surface of the upper portion of the transmission shaft 79 (second opening 72A) and substantially the axial center portion of the transmission shaft 79. The supply hole 72 is arranged on the rotationally downstream side of the transmission shaft 79, as compared to the supply hole 42 of the embodiment shown in FIG. 5A and FIG. 5B. The supply hole 72 is formed by a drilled hole or the like.

The groove 71 is formed as an upright groove provided in an axial direction, in the outer circumferential surface of the transmission shaft 79. A first opening 71A is formed by having the lower end portion of the groove 71 overlapped with the upper portion of the lubricating oil passage 2D in the vertical direction. The groove 71 is arranged closer to the supply hole 72 as compared to the groove 41 of the embodiment shown in FIG. 5A and FIG. 5B. A lateral hole serving as a communication path 73 is provided from the upper end portion of the groove 71 toward the start portion of the supply hole 72. In the present example, the first opening 71A is a part of the groove 71, and by having the groove 71 overlapped with the lubricating oil passage 2D in the axial direction, the first opening 71A is formed.

The following describes the shape of the groove 71, with reference to FIG. 8C.

The groove 71 is formed in a substantially L-shape in plan view as is the case of the upright groove 61C shown in FIG. 8C. The groove 71 has a wall portion 71B forming a bottom of the groove 71, and a side wall 71C formed substantially perpendicularly to the wall portion 71B, which is provided only to the rotation-upstream end of the wall portion 71B. That is, the groove 71 is formed in a substantially L-shape in plan view. The communication path 73 is a lateral hole formed in a radial direction of the transmission shaft 79 from the wall portion 71B of the groove 71.

With at least one side wall 71C formed substantially perpendicularly to the wall portion 71B, the lubricating oil taken into the groove 71 from the first opening 71A forms a vortex at a corner portion formed by the wall portion 71B and the side wall 71C of the groove 71. Since the lubricating oil tends to stay at the corner portions of the groove 71, leakage of the lubricating oil from the groove 71 between the transmission shaft hole 2C and the transmission shaft 79 can be reduced, and the oil pressure of the lubricating oil flowing in the groove 71 can be maintained.

Further, the communication path 73 is provided as a lateral hole from the wall portion 71B of the groove 71 to the inside of the transmission shaft 79. Therefore, the communication passage 73 can be easily formed without a need for complicated processing.

Since the groove 71 and the communication path 73 of the present embodiment each has a total length longer than the oil passage 40 of the embodiment shown in FIG. 5A and FIG. 5B, by providing the second opening 72A in a position rotated and displaced from the position of the first opening 71A, by a desirable angle between approximately 90 to 135 degrees (approximately 120 degrees in the present embodiment) towards the downstream side of the rotation of the transmission shaft 79, the lubricating oil can be sprayed from the second opening 72A onto the control rack 20, at a desirable position.

As described, by making the total length of the supply hole 72 short, as compared to the oil passage 40 of the embodiment shown in FIG. 5A and FIG. 5B, machining is made easier, and the life of a machining tool is made longer.

Figure 10A:
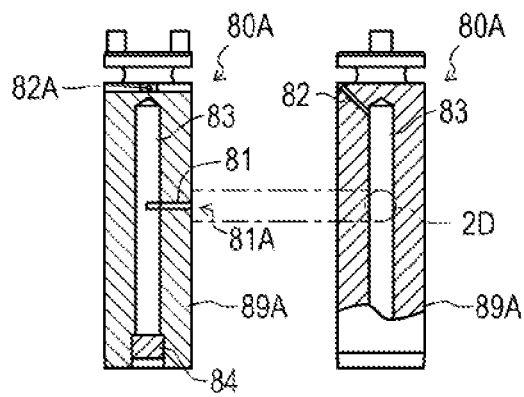
FIG. 10A is a diagram showing a structure of an oil passage of a fifth embodiment.
Figure 10B:
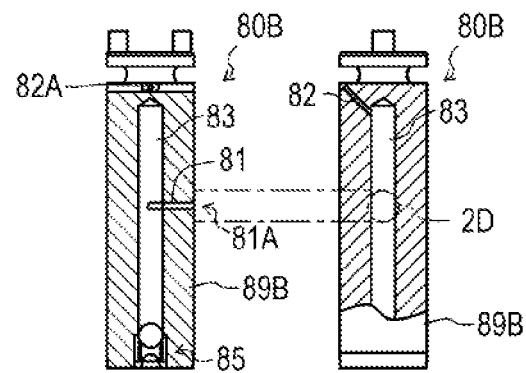
FIG. 10B is a diagram showing a structure of an oil passage of a sixth embodiment.
Figure 10C:
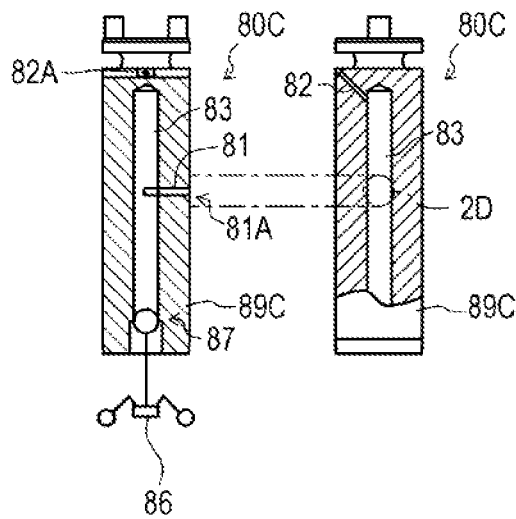
FIG. 10C is a diagram showing a structure of an oil passage of a seventh embodiment.

The following describes structures of transmission shafts of embodiments with reference to FIG. 10A through FIG. 10C.

In an oil passage provided to a transmission shaft of each embodiment shown in FIG. 10A through FIG. 10C, the first opening is structured by a lateral hole provided substantially toward the axial center portion of the transmission shaft, instead of a groove provided in the outer circumferential surface of the transmission shaft, and the communication path communicating the lateral hole with the supply hole is formed by an upright hole provided from a bottom portion of the transmission shaft, along the axis.

A structure of a transmission shaft 89A is described with reference to FIG. 10A. The transmission shaft 89A is a fifth embodiment related to the transmission shaft of the present invention. The transmission shaft 89A has an oil passage 80A formed therein, through which passage the lubricating oil pressure-fed to the lubricating oil passage 2D partially passes.

It should be noted that, FIG. 10A provides a front view (a view seen from the side of a later-described second opening 82A) and a side view (a view seen from a side of a later-described first opening 81A) of the structure of the transmission shaft 89A.

The supply hole 82 is formed substantially towards the axial center portion from the second opening 82A provided in the outer circumferential surface of the upper portion of the transmission shaft 89A, nearby the control rack 20. The start portion of the supply hole 82 (end portion on the side of the axis of the transmission shaft 89A) is communicated with a later-described upright hole 83.

The transmission shaft 89A is provided with a lateral hole 81 from its outer circumferential surface toward its axis. The first opening 81A is formed by arranging the lateral hole 81 so as to overlap with the lubricating oil passage 2D. The transmission shaft 89A is provided with the upright hole 83 from its bottom surface, along the axis. The upright hole 83 is provided so as to penetrate the bottom portion of the transmission shaft 89, and the bottom portion is closed by a sealing plug 84. The end portion of the lateral hole 81 is communicated with a midway portion of the upright hole 83.

By closing the bottom portion of the upright hole 83 with the sealing plug 84, the oil pressure of the lubricating oil flowing in the upright hole 83 can be maintained. Further, the upright hole 83 is provided from the bottom surface of the transmission shaft 89A to the inside of the transmission shaft 89A. Therefore, the upright hole 83 can be easily formed without a need for complicated processing.

A structure of a transmission shaft 89B is described with reference to FIG. 10B. The transmission shaft 89B is a sixth embodiment related to the transmission shaft of the present invention. The transmission shaft 89B has an oil passage SOB formed therein, through which passage the lubricating oil pressure-fed to the lubricating oil passage 2D partially passes.

It should be noted that, FIG. 10B provides a front view (a view seen from the side of a later-described second opening 82A) and a side view (a view seen from a side of a later-described first opening 81A) of the structure of the transmission shaft 89B.

The oil passage 80B is formed by providing a pressure regulating valve 85 instead of the sealing plug 84 in the structure of the oil passage 80A of the embodiment shown in FIG. 10A. With the pressure regulating valve 85 at the bottom portion of the upright hole 83, if the oil pressure of the lubricating oil flowing inside the oil passage 80B is too high, part of the oil is discharged outside from the bottom portion of the transmission shaft 89B. Thus, with the pressure regulating valve 85, the amount of lubricating oil sprayed to the control rack 20 can be made constant.

A structure of a transmission shaft 89C is described with reference to FIG. 10C. The transmission shaft 89C is a seventh embodiment related to the transmission shaft of the present invention. The transmission shaft 89C has an oil passage 80C formed therein, through which passage the lubricating oil pressure-fed to the lubricating oil passage 2D partially passes.

It should be noted that, FIG. 10C provides a front view (a view seen from the side of a later-described second opening 82A) and a side view (a view seen from a side of a later-described first opening 81A) of the structure of the transmission shaft 89C.

The oil passage 80C is formed by providing a throttle valve 87 which performs an open/close operation by using a centrifugal force of a centrifugal weight 86, instead of the sealing plug 84 in the structure of the oil passage 80A of the embodiment shown in FIG. 10A. The throttle valve 87 is structured so as to open and close when its valve body is slid by a change in a centrifugal force of the centrifugal weight 86 due to the rotational speed of the transmission shaft 89C. In the present embodiment, the valve is closed when the rotational speed of the transmission shaft 89C becomes high. By structuring the valve so that it opens and closes according to the rotational speed of the transmission Shaft 89C, the amount of lubricating oil sprayed to the control rack 20 can be made constant, irrespective of the rotational speed of the transmission shaft 89C, i.e., the rotational speed of the diesel engine 30.

Figure 11A:
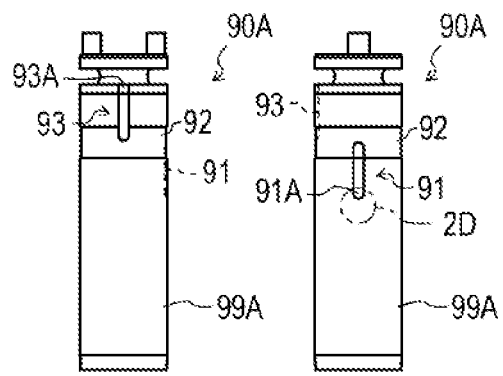
FIG. 11A is a diagram showing a structure of an oil passage of an eighth embodiment.
Figure 11B:
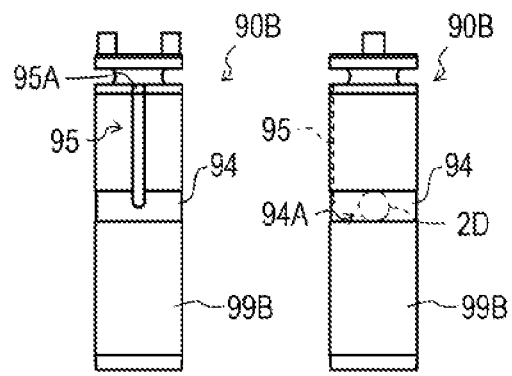
FIG. 11B is a diagram showing a structure of an oil passage of a ninth embodiment.

The following describes structures of transmission shafts of embodiments with reference to FIG. 11A and FIG. 11B.

An oil passage provided to a transmission shaft of each embodiment shown in FIG. 11A and FIG. 11B is structured by a groove provided in the outer circumferential surface of the transmission shaft.

A structure of a transmission shaft 99A is described with reference to FIG. 11A. The transmission shaft 99A is an eighth embodiment related to the transmission shaft of the present invention. The transmission shaft 99A has an oil passage 90A formed therein, through which passage the lubricating oil pressure-fed to the lubricating oil passage 2D partially passes.

It should be noted that, FIG. 11A provides a front view (a view seen from the side of a later-described second opening 93A) and a side view (a view seen from a side of a later-described first opening 91A) of the structure of the transmission shaft 99A.

The first opening 91A is structured by having the lubricating oil passage 2D partially overlapped in the axial direction with an upright groove 91 provided in the outer circumferential surface of the transmission shaft 99A. In the upper end portion of the upright groove 91, a circumferential groove 92 provided along the circumferential direction of the transmission shaft 99A is arranged so that its lower portion is overlapped in the axial direction. In the upper portion of the circumferential groove 92, an upright groove 93 provided toward the outer circumferential surface of the upper portion of the transmission shaft 99A is arranged so that its lower portion is overlapped in the axial direction. In the present example, the first opening 91A is a part of the upright groove 91, and by having the upright groove 91 overlapped with the lubricating oil passage 2D in the axial direction, the first opening 91A is formed.

In the above-described structure, the lubricating oil taken in from the first opening 91A is taken into the circumferential groove 92 through the upright groove 91. The lubricating oil taken into the circumferential groove 92 flows into the upright groove 93 and is sprayed to the control rack 20, from the second opening 93A constituting the upper end portion of the upright groove 93 (between the transmission shaft 99A and the transmission shaft hole 2C).

By making the depth of the groove 93 shallow for example, the pressure of the lubricating oil flowing in the upright groove 93 is set to a pressure that enables spraying of the lubricating oil to the control rack 20.

Thus, by structuring the oil passage with a groove formed in the outer circumferential surface of the transmission shaft 99A, the oil passage 90A can be easily formed.

A structure of a transmission shaft 99B is described with reference to FIG. 11B. The transmission shaft 99B is a ninth embodiment related to the transmission shaft of the present invention. The transmission shaft 99B has an oil passage 90B formed therein, through which passage the lubricating oil pressure-fed to the lubricating oil passage 2D partially passes.

It should be noted that, FIG. 11B provides a front view (a view seen from the side of a later-described second opening 95A) and a side view (a view seen from a side of a later-described first opening 94A) of the structure of the transmission shaft 99B.

The first opening 94A is structured by arranging a circumferential groove 94 in the circumferential direction of the transmission shaft 99B so as to overlap with the lubricating oil passage 2D in the axial direction. In the upper portion of the circumferential groove 94, an upright groove 95 provided toward the outer circumferential surface of the upper portion of the transmission shaft 99B is arranged so as to partially overlap in the axial direction. In the present embodiment, the first opening 91A is formed by overlapping the circumferential groove 94 with the lubricating oil passage 2D, in the axial direction.

In the above-described structure, the lubricating oil taken in from the first opening 94A is taken into the upright groove 95 through the circumferential groove 94. The lubricating oil taken into the upright groove 95 is sprayed to the control rack 20, from the second opening 95A constituting the upper end portion of the upright groove 95 (between the transmission shaft 99B and the transmission shaft hole 2C).

By making the depth of the groove 95 shallow for example, the pressure of the lubricating oil flowing in the upright groove 95 is set to a pressure that enables spraying of the lubricating oil to the control rack 20.

Thus, by structuring the oil passage with a groove formed in the outer circumferential surface of the transmission shaft 99B, the oil passage 90B can be easily formed. Further, since the lower portion of the circumferential groove 94 is always communicated with the lubricating oil passage 2D, the oil is always injected to the control rack 20.

A structure of a transmission shaft 109 is described with reference to FIG. 12A and FIG. 12B. The transmission shaft 109 is a tenth embodiment related to the transmission shaft of the present invention. The transmission shaft 109 has an oil passage 100 formed therein, through which passage the lubricating oil pressure-fed to the lubricating oil passage 2D partially passes.

Figures 12A, 12B:
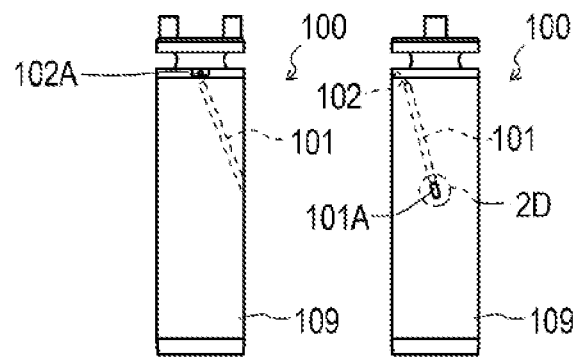
FIG. 12A and FIG. 12B are diagrams showing a structure of an oil passage of a tenth embodiment.

It should be noted that, FIG. 12A provides a front view (a view seen from the side of a later-described second opening 102A) of the structure of the transmission shaft 109, whereas FIG. 12B provides a side view (a view seen from a side of a later-described first opening 101A) of the structure of the transmission shaft 109.

The supply hole 102 is formed substantially towards the axial center portion from the second opening 102A provided in the outer circumferential surface of the upper portion of the transmission shaft 109A. The first opening 101A is structured by providing a through hole 101 penetrating from the outer circumferential surface of the transmission shaft 109 capable of communicating with the lubricating oil passage 2D to a start portion of the supply hole 102 (an end portion on the side of the axis of the transmission shaft 109). The start portion of the supply hole 102 is communicated with an end portion of the through hole 101. Thus, since the oil passage 100 is formed inside the transmission shaft 109, the oil pressure of the lubricating oil flowing in the oil passage 100 can be maintained.

The oil passage of each of the above-described embodiments are structured by providing a groove or a hole to the transmission shaft 109; however, the oil passage is not limited to the above. For example, the oil passage may be formed by providing a groove or a hole to the pump housing 2 rotatably supporting the transmission shaft 109.

Figure 13A:
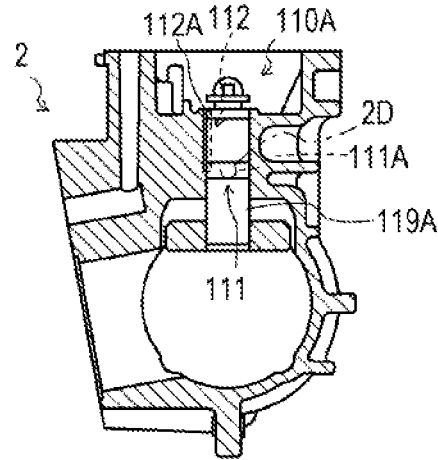
FIG. 13A is a diagram showing a structure of an oil passage of an eleventh embodiment.
Figure 13B:
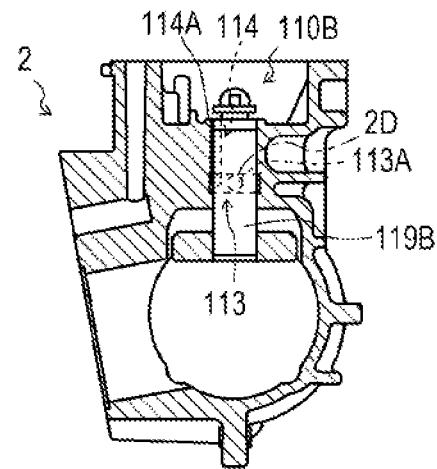
FIG. 13B is a diagram showing a structure of an oil passage of a twelfth embodiment.
Figure 13C:
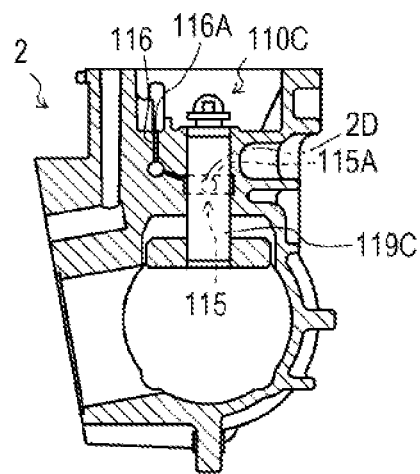
FIG. 13C is a diagram showing a structure of an oil passage of a thirteenth embodiment.

The following describes the structure of the transmission shaft and the pump housing 2 of each of embodiments shown in FIG. 13A through FIG. 13C.

The oil passage of each of the embodiments shown in FIG. 13A through FIG. 13C is structured by providing a groove or a hole to the transmission shaft and the pump housing 2, or only to the pump housing 2.

A structure of an eleventh embodiment of the oil passage formed to the transmission shaft 119A and the pump housing 2 is described with reference to FIG. 13A. The transmission shaft 119A and the pump housing 2 have an oil passage 110A through which the lubricating oil pressure-fed to the lubricating oil passage 2D partially passes. It should be noted that, in side views of FIG. 13A, the structures of the transmission shaft 119A and the pump housing 2 are illustrated as a partial cross-sectional view of the pump housing 2, viewed from the front-rear direction.

The first opening 111A is structured by arranging a circumferential groove 111 in the circumferential direction, in the outer circumferential surface of the transmission shaft 119A so as to overlap with the lubricating oil passage 2D in the axial direction. An upright groove 112 is provided in the inner circumferential surface of the transmission shaft hole 2C so as to partially overlap in the axial direction, with the upper portion of the circumferential groove 111. The upright groove 112 is formed from the upper portion of the circumferential groove 111 toward the bottom surface of the rack chamber 5. In the present embodiment, the first opening 111A is formed by overlapping the circumferential groove 111 with the lubricating oil passage 2D, in the axial direction.

In the above-described structure, the lubricating oil taken in from the first opening 111A is taken into the upright groove 112 through the circumferential groove 111. The lubricating oil taken into the upright groove 112 is sprayed to the control rack 20, from the second opening 112A constituting the upper end portion of the upright groove 112 (between the transmission shaft 119A and the transmission shaft hole 2C).

A structure of a twelfth embodiment of the oil passage formed to the pump housing 2 is described with reference to FIG. 13B. The pump housing 2 has an oil passage 110B through which the lubricating oil pressure-fed to the lubricating oil passage 2D partially passes. It should be noted that, in side views of FIG. 13A, the structures of the transmission shaft 119B and the pump housing 2 are illustrated as a partial cross-sectional view of the pump housing 2, viewed from the front-rear direction.

The first opening 113A is structured by arranging a circumferential groove 113 in the circumferential direction, in the inner circumferential surface of the transmission shaft hole 2C so as to partially overlap with the lubricating oil passage 2D in the vertical direction. An upright groove 113 is provided in the inner circumferential surface of the transmission shaft hole 2C so as to partially overlap in the vertical direction, with the upper portion of the circumferential groove 114. The upright groove 114 is formed from the upper portion of the circumferential groove 113 toward the bottom surface of the rack chamber 5. In the present embodiment, the first opening 113A is formed by overlapping the circumferential groove 113 with the lubricating oil passage 2D, in the axial direction.

In the above-described structure, the lubricating oil taken in from the first opening 113A is taken into the upright groove 114 through the circumferential groove 113. The oil taken into the upright groove 114 is sprayed to the control rack 20, from the second opening 114A constituting the upper end portion of the upright groove 114 (between the transmission shaft 119B and the transmission shaft hole 2C).

A structure of a thirteenth embodiment of the oil passage formed to the pump housing 2 is described with reference to FIG. 13C. The pump housing 2 has an oil passage 110C through which the lubricating oil pressure-fed to the lubricating oil passage 2D partially passes. It should be noted that, in side views of FIG. 13A, the structures of the transmission shaft 119C and the pump housing 2 are illustrated as a partial cross-sectional view of the pump housing 2, viewed from the front-rear direction.

The first opening 115A is structured by arranging a circumferential groove 115 in the circumferential direction, in the inner circumferential surface of the transmission shaft hole 2C so as to partially overlap with the lubricating oil passage 2D in the axial direction. A supply hole 116 is provided inside the pump housing 2, from the circumferential groove 115 toward the bottom surface of the rack chamber 5. In the present embodiment, the first opening 115A is formed by overlapping the circumferential groove 115 with the lubricating oil passage 2D, in the axial direction.

In the above-described structure, the lubricating oil taken in from the first opening 115A is taken into the supply hole 116 through the circumferential groove 115. The oil taken into the supply hole 116 is sprayed to the control rack 20, from the second opening 116A constituting the upper end portion of the supply hole 116.

It should be noted that the a through hole may be provided from the side of the governor housing 27 directly to the supply hole 116 provided inside the pump housing 2, without the lubricating oil passage 2D intervened.

Figure 14:
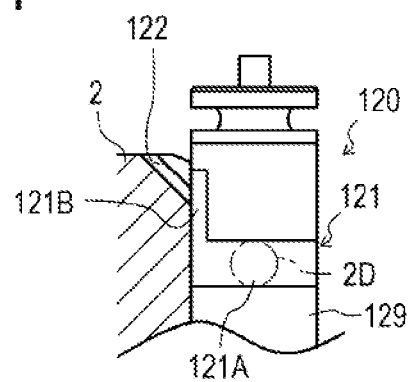
FIG. 14 is a diagram showing a structure of an oil passage of a fourteenth embodiment.

A structure of a fourteenth embodiment of the oil passage formed to the pump housing 2 is described with reference to FIG. 14. The pump housing 2 has an oil passage 120 through which the lubricating oil pressure-fed to the lubricating oil passage 2D partially passes. It should be noted that, in side views of FIG. 14, the structures of the transmission shaft 129 and the pump housing 2 are illustrated as a partial cross-sectional view of the pump housing 2, viewed from the front-rear direction.

The first opening 121A is structured by arranging a circumferential groove 121 in the circumferential direction, in the outer circumferential surface of the transmission shaft 129 so as to partially overlap with the lubricating oil passage 2D in the axial direction. The circumferential groove 121B is provided with an expanded portion 121B in which the groove width is widened in the axial direction. In the pump housing 2, a supply hole 122 capable of communicating with the upright portion 121B is provided. The supply hole 122 penetrates a surface on the side of the transmission shaft hole 2C of the pump housing 2 and the bottom surface constituting the rack chamber 5, at a desirable inclination angle in the pump housing 2. In the present embodiment, the first opening 121A is formed by overlapping the circumferential groove 121 with the lubricating oil passage 2D, in the axial direction.

As hereinabove described, an oil passage can be also formed by forming a groove or a hole in the pump housing 2. In cases of forming a groove or a hole in the pump housing 2, the groove or the hole is formed by casting. Therefore, there is no need for machining such as cutting, and the groove or a hole can be easily formed.

INDUSTRIAL APPLICABILITY

The present invention is applicable to a fuel injection pump.

REFERENCE SIGNS LIST 1 fuel injection pump
2 pump housing
2A governor flange
2C transmission shaft hole
2D lubricating oil passage
3 pump head
4 cam chamber
5 rack chamber
15 distribution shaft
20 control rack
30 diesel engine
32 lubricating oil pump
40 oil passage
41 groove
41A first opening
41B wall portion
41C side wall
42 supply hole
42A second opening
43 communication path
49 transmission shaft

The invention claimed is:

1. A fuel injection pump to be provided in an engine, the fuel injection pump comprising:
   a control rack configured to adjust a fuel injection amount;
   a transmission shaft rotatably supported by a transmission shaft hole formed in a pump housing; and
   a lubricating oil passage formed in the pump housing,
   wherein the transmission shaft defines:
      an oil passage configured such that the lubricating oil flowing through lubricating oil passage partially passes through the oil passage,
      a first opening of the oil passage that is in communication with the lubricating oil passage, and
      a second opening of the oil passage that is formed on an outermost circumferential surface of an upper portion of the transmission shaft, the second opening configured to output the lubricating oil to the control rack.

2. The fuel injection pump according to claim 1, wherein the oil passage includes:
   a groove formed in the outer circumferential surface of the transmission shaft in an axial direction thereof, the groove including the first opening;
   a communication path opened on a wall portion of the groove, and formed in a radial direction of the transmission shaft; and
   a supply hole communicated with the communication path and formed from substantially an axial center portion of the transmission shaft to the second opening.

3. The fuel injection pump according to claim 2, wherein the groove has at least one side wall formed perpendicular to the wall portion.

4. The fuel injection pump according to claim 3, wherein a lower end portion of an open portion of the groove is formed in a substantially U-shape.

5. The fuel injection pump of claim 1, wherein the second opening is formed in a recess of an upper edge of the transmission shaft.

6. The fuel injection pump of claim 2, wherein the first opening is defined by an overlap of a bottom portion of the groove and the lubricating oil passage.

7. A fuel injection pump comprising:
   a pump housing that defines:
      a shaft hole; and
      a first passage in communication with the shaft hole, the first passage configured to pressure-feed oil through at least a portion of the pump housing;
   a pump head coupled to the pump housing such that a rack chamber is defined between the pump housing and the pump head;
   a control rack disposed within the rack chamber, the control rack configured to adjust a fuel injection amount;
   a transmission shaft disposed in the pump housing and extending from the pump housing to the rack chamber though the shaft hole, the transmission shaft defining:
      a second passage that defines a flow path of the oil from the first passage to the control rack;
   wherein the second passage comprises:
      a groove formed in an axial direction of an outer circumferential surface of the transmission shaft, the groove includes:
         a first opening defined by an overlap of the groove and the first passage; and
         a second opening is formed on the outer circumferential surface of an upper portion of the transmission shaft, the second opening configured to output the oil onto the control rack.

8. The fuel injection pump according to claim 7, wherein the second passage includes:
a communication path opened on a wall portion of the groove, and formed in a radial direction of the transmission shaft; and
a supply hole communicated with the communication path and formed from substantially an axial center portion of the transmission shaft to the second opening.

9. The fuel injection pump according to claim 8, wherein the groove has at least one side wall formed perpendicular to the wall portion.

10. The fuel injection pump of claim 8, wherein the groove comprises:
a bottom portion that includes the first opening; and
a top portion, where the communication path extends from the top portion of the groove to substantially the axial center portion of the transmission shaft.

11. The fuel injection pump of claim 10, wherein
the top portion of the groove is positioned above the first passage; and
the bottom portion of the groove is aligned with the first passage.

12. The fuel injection pump according to claim 10, wherein the bottom portion of the groove is formed in a substantially U-shape.

13. The fuel injection pump of claim 8, wherein a cross-sectional area of the supply hole is less than a cross-sectional area of the communication path such that the oil exiting the second opening is sprayed on the control rack.

14. The fuel injection pump of claim 7, wherein the second opening is angularly disposed relative to the first opining by an angle between 90 to 135 degrees.

15. A fuel injection pump comprising:
a pump housing that defines:
a shaft hole; and
a first passage in communication with the shaft hole, the first passage configured to pressure-feed oil through at least a portion of the pump housing;
a pump head coupled to the pump housing such that a rack chamber is defined between the pump housing and the pump head;
a control rack disposed within the rack chamber, the control rack configured to adjust a fuel injection amount;
a transmission shaft disposed in the pump housing and extending from the pump housing to the rack chamber though the shaft hole, the transmission shaft defining:
a recess formed at an upper edge of an outer circumferential surface of the transmission shaft; and
a second passage that defines a flow path of the oil from the first passage to the control rack;
wherein the second passage comprises:
a first opening in communication with the first passage; and
a second opening formed in the recess of the transmission shaft, the second opening configured to output the oil onto the control rack.

16. The fuel injection pump according to claim 15, wherein the upper edge is defined by an intersection of a sidewall of the transmission shaft and an upper surface of the transmission shaft.

17. The fuel injection pump according to claim 15, wherein the recess extends from the outer circumferential surface of the transmission shaft towards an axial center portion of the transmission shaft.

18. The fuel injection pump according to claim 15, wherein the second passage further includes:
a groove formed in the outer circumferential surface of the transmission shaft in an axial direction thereof, the groove including the first opening;
a communication path opened on a wall portion of the groove, and formed in a radial direction of the transmission shaft; and
a supply hole communicated with the communication path and formed from substantially an axial center portion of the transmission shaft to the second opening.

19. The fuel injection pump of claim 18, wherein the first opening is defined by an overlap of a bottom portion of the groove and the first passage.

20. The fuel injection pump of claim 18, wherein the groove comprises:
a bottom portion that includes the first opening; and
a top portion, where the communication path extends from the top portion of the groove to substantially the axial center portion of the transmission shaft.

* * * * *